United States Patent
Somasundaram et al.

(10) Patent No.: US 8,637,241 B2
(45) Date of Patent: Jan. 28, 2014

(54) MICRORNAS (MIRNA) AS BIOMARKERS FOR DIAGNOSING DIFFERENT GRADES OF GLIOMAS AND PATHWAYS OF GLIOMA PROGRESSION

(75) Inventors: Kumaravel Somasundaram, Bangalore (IN); Soumya Aliga Mahabala Rao, Bangalore (IN); Vani Santosh, Bangalore (IN)

(73) Assignees: Department of Biotechnology, New Delhi (IN); Indian Institute of Sciences, Bangalore (IN)

( * ) Notice: Subject to any disclaimer, the term of this patent is extended or adjusted under 35 U.S.C. 154(b) by 160 days.

(21) Appl. No.: 13/076,834

(22) Filed: Mar. 31, 2011

(65) Prior Publication Data

US 2011/0256547 A1     Oct. 20, 2011

(30) Foreign Application Priority Data

Apr. 1, 2010   (IN) .............................. 810/DEL/2010

(51) Int. Cl.
*C12Q 1/68*      (2006.01)
*C12N 15/11*    (2006.01)
*C07H 21/02*    (2006.01)
*C07H 21/04*    (2006.01)

(52) U.S. Cl.
USPC ........................ 435/6.1; 435/6.11; 536/23.1

(58) Field of Classification Search
None
See application file for complete search history.

*Primary Examiner* — James Martinell
(74) *Attorney, Agent, or Firm* — Venable LLP; Nancy J. Axelrod; Keith G. Haddaway (57) ABSTRACT

This invention relates to a method for detecting, (i) malignant astrocytoma from normal brain tissue (ii) glioblastoma and anaplastic astrocytoma (iii) primary glioblastoma and secondary glioblastoma (iv) progressive pathway and denovo pathway comprises determining the level of expression of miRNAs listed in table 2, 3, 4, 5, wherein a higher or lower level of expression of miRNAs in the test sample as compared to the control sample differentiates and kit for characterizing a) malignant astrocytoma from normal brain tissue cell comprising reagent capable of specifically detecting the level of expression of the genes of miRNAs and instructions for using said kit for characterizing malignant astrocyoma from normal brain tissue cells b) glioblastoma from anaplastic astrocytoma comprising reagent capable of specifically detecting the level of expression of the genes of miRNAs and instructions for using said kit for characterizing glioblastoma from anaplastic astrocyoma c) primary glioblastoma from secondary glioblastoma comprising reagent capable of specifically detecting the level of expression of the genes of miRNAs and instructions for using said kit for characterizing primary glioblastoma from secondary glioldastoma, d) progressive pathway from denovo pathway comprising reagent capable of specifically detecting the level of expression of the genes of miRNAs and instructions for using said kit for characterizing progressive pathway from denovo pathway.

9 Claims, 3 Drawing Sheets
(3 of 3 Drawing Sheet(s) Filed in Color)

MICRORNAS (MIRNA) AS BIOMARKERS FOR DIAGNOSING DIFFERENT GRADES OF GLIOMAS AND PATHWAYS OF GLIOMA PROGRESSION

FIELD OF INVENTION

This invention relates to a MicroRNAs (miRNA) as biomarkers for detecting different grades of gliomas and pathways of glioma progression.

BACKGROUND OF INVENTION

Gliomas are the most common primary brain tumors and occur at an incidence of almost 12 per 100,000 people (Landis et al., 1999). Diffuse astrocytoma may be classified (as per WHO classification) as lower-grade diffuse (DA; Grade II), anaplastic (AA; Grade III) and glioblastoma (Grade IV; GBM), in the order of increasing malignancy (Mischel et al., 2001). Currently, these classifications are based on the observed histopathological characteristics of the tumor, which are sometimes subjective and inconsistent. GBM constitutes more than 80% of malignant gliomas (DeAngelis et al., 2001) and patients with GBM have a median survival of less than one year. Current treatments, including surgery, radiation therapy, and chemotherapy, unfortunately have not changed the natural history of these incurable neoplasms; and the prognosis of patients with GBMs has not improved significantly in the past 30 years (Davis et al., 1998). To find new diagnostic and therapeutic strategies, a better understanding of the biological pathway(s) leading to glial tumorigenesis is warranted.

Astrocytoma development is known to involve accumulation of a series of genetic alterations (Nagane et al., 1997) similar to other cancers. Identification of many of the genes involved in astrocytoma development, using standard molecular approaches, has helped to understand the process of astrocytoma genesis and progression (Louis and Gusella, 1995). Frequent amplification of epidermal growth factor receptor (EGFR) (Hill et al., 1999; Brock and Bower, 1997), platelet derived growth factor receptor (PDGFR) (Hermanson et al., 1992; Hermanson et al., 1996; Maxwell et al., 1990; Westermark et al., 1995; Fleming et al., 1992), amplification of chromosome 12q region, which carries the cdk4 gene (Nagane et al., 1997; Hill et al., 1999) and alterations in chromosomes 1p, 9p, 10, 17p, 19q, and 22q have frequently been found in these tumors. In addition, mutations in the tumor suppressor gene p53 were found to be associated with chromosome 17p alterations in low grade and progressive astrocytoma (Maher et al., 2001; Phatak et al., 2002). Inactivation of the cdk inhibitor p16 INK4a residing in chromosome 9p, is very common in sporadic astrocytoma, occurring in 50-70% of high-grade gliomas and 90% of GBM cell lines (James et al., 1991; Olopade et al., 1992). LOH in chromosome 10 is one of the most frequent alterations in GBM and is accompanied by the loss of PTEN/MMAC gene (Hill et al., 1999; Li et al., 1997).

Despite all this information about astrocytoma, our understanding of astrocytoma development is not sufficient enough to improve prognosis for GBM patients. A more global, systematic understanding of expression patterns of various genes and their downstream gene products in astrocytoma will hopefully provide new diagnostic and therapeutic targets. Towards this, a number of studies have reported the gene expression profile of astrocytoma (Liau et al., 2000; Sallinen et al., 2000; Rickman et al., 2001; Ljubimova et al., 2001; Watson et al., 2001; Tanwar et al., 2002; Fathallah-Shaykh et al., 2002; Nutt et al., 2003; Wang et al., 2003; Godard et al., 2003).

It is also desirable to be able to target specific therapeutic modalities to pathogenetically distinct tumor types to maximize efficacy and minimize toxicity to the patient. (Golub et al., 1999; Kudoh et al., 2000). Previously, cancer classification has been based primarily on the morphological appearance of tumor cells. But this has serious limitations, because tumors with similar histopathological appearance can follow significantly different clinical courses and show different responses to therapy. For example, based on histopathological appearance, astrocytoma grade IV cannot consistently be distinguished from astrocytoma grade III. Immunophenotyping for brain tumors has defined and refined diagnosis, e.g., distinguishing oligoastrocytoma from astrocytomas, and high-grade from low-grade astrocytomas. However, differential protein expression (GFAP, vimentin, synaptophysin, nestin) has not helped to improve therapeutic approaches. Prediction of transitions from low- to high-grade astrocytomas is difficult to make with currently available markers (De Girolami et al., 1994).

(Tews and Nissen, 1998-99) reported that immunohistochemical detection of various cancer-associated markers failed to reveal significant differential expression patterns among primary and secondary glioblastomas and precursor tumors; there was also no intra-individual constant expression pattern during glioma progression or correlation with malignancy.

GBMs have been further subdivided into the primary or secondary GBM subtypes on the basis of clinical and molecular profile. Primary GBMs (pGBM) account for the most of GBM cases, occurring in older patients, while secondary GBMs (sGBM) are quite rare and tend to occur in patients below the age of 45 year. Primary GBM presents in an acute de novo manner with no evidence of a prior symptoms or antecedent lower grade pathology. In contrast, secondary GBM results from the progressive malignant transformation of a DA or AA (Ohgaki and Kleihues, 2007). Remarkably, despite their distinct clinical profiles, primary and secondary GBMs are morphologically and clinically indistinguishable as reflected by an equally poor prognosis when adjusted for patient age (Ohgaki and Kleihues, 2007). However, although these GBM subtypes achieve a common clinical endpoint, recent studies have identified markedly different transcriptional patterns and DNA copy number variations between them (Furnari et al., 2007, Somasundaram et al., 2005). These molecular distinctions make obvious the need to change the current standardized clinical management of these truly distinct entities toward one of rational application of targeted therapies directed towards appropriate molecular subclasses. Furthermore, sGBMs most often have areas of grade III tumor within them and it is necrosis and/or microvascular proliferation that histologically confers the diagnosis of GBM in these tumors. In the event that these areas are missed due to sampling problems, one would still consider the tumor as an AA tumor. It is in such instances that molecular sub-classification proves to be of immense use.

Through miRNA gene expression profiling and real-time quantitative PCR, we have found several differentially regulated miRNAs as diagnostic markers to differentiate, (1) Malignant astrocytoma and Normal brain, (2) Glioblastoma and Anaplastic Astrocytoma, (3) Secondary Glioblastoma and Primary Glioblastoma, (4) Progressive pathway and de novo pathway, and in addition to identifying grade specific miRNAs, inventors identified a 24 miRNA expression signature set that precisely differentiated GBM from AA with an accuracy rate of 95%. By this they would be able to administer appropriate treatment by classifying GBM and AA. These and other benefits are provided by the present invention.

Currently, the classification of grades of Glioma, types of GBMs is based on the observed histopathological characteristics of the tumor.

The classification of grades based on the observed histopathological characteristics of the tumor, are sometimes subjective and inconsistent. But this has serious limitations, because tumors with similar histopathological appearance can follow significantly different clinical courses and show different responses to therapy. For example, based on histopathological appearance, astrocytoma grade IV cannot consistently be distinguished from astrocytoma grade III. Due to the inconsistent classification of grades there is probability of administering inappropriate treatment, which may further decrease the patient's chances of survival. GBM constitutes more than 80% of malignant gliomas (DeAngelis et al., 2001) and patients with GBM have a median survival of less than one year. Current treatments, including surgery, radiation therapy, and chemotherapy, unfortunately have not changed the natural history of these incurable neoplasms; and the prognosis of patients with GBMs has not improved significantly in the past 30 years.

In order to obtain a histology independent miRNA expression signature to differentiate. GBM from AA tumors, we have analyzed the expression of 756 miRNAs by microarray in 13 AA and 29 GBM tumor samples. In addition to identifying grade specific miRNAs, we were able to identify a 24 miRNA expression signature set that precisely differentiated GBM from AA with an accuracy rate of 95%.

Through microarray and real-time quantitative PCR, we found several differentially regulated miRNAs to be specific markers for distinguishing and diagnosing (1) Malignant Astrocytoma and Normal Brain sample, (2) Glioblastoma and Anaplastic astrocytoma, (3) Secondary Glioblastoma and Primary Glioblastoma, (4) Progressive pathway and de novo pathway, thus, to be able to administer appropriate treatment. The method can also be applied to monitor the effectiveness of anti-cancer treatments.

OBJECTS OF INVENTION

The main object of this invention is to develop a process for detecting different grades of gliomas and pathways of glioma progression.

Other object is to develop a process using Micro RNAs as biomarkers for the detection.

Another object is to develop a process which can accurately classify different grades of glioma.

Yet another object is to develop a process which is useful in differentiating
a) Malignant Astrocytoma and normal brain sample
b) Glioblastoma and Anaplastic Astrocytoma
c) Secondary glioblastoma and primary Glioblastoma
d) Progressive pathway and denovo pathway.

STATEMENT OF INVENTION

According to this invention there is provided a method for detecting, (i) malignant astrocytoma from normal brain tissue (ii) glioblastoma and anaplastic astrocytoma (iii) primary glioblastoma and secondary glioblastoma (iv) progressive pathway and denovo pathway comprises determining the level of expression of miRNAs listed in table 2, 3, 4, 5, wherein a higher or lower level of expression of miRNAs in the test sample as compared to the control sample differentiates and kit for characterizing a) malignant astrocytoma from normal brain tissue cell comprising reagent capable of specifically detecting the level of expression of the genes of miRNAs and instructions for using said kit for characterizing malignant astrocyoma from normal brain tissue cells b) glioblastoma from anaplastic astrocytoma comprising reagent capable of specifically detecting the level of expression of the genes of miRNAs and instructions for using said kit for characterizing glioblastoma from anaplastic astrocyoma c) primary glioblastoma from secondary glioblastoma comprising reagent capable of specifically detecting the level of expression of the genes of miRNAs and instructions for using said kit for characterizing primary glioblastoma from secondary glioldastoma, d) progressive pathway from denovo pathway comprising reagent capable of specifically detecting the level of expression of the genes of miRNAs and instructions for using said kit for characterizing progressive pathway from denovo pathway.

BRIEF DESCRIPTION OF ACCOMPANYING DRAWINGS

The patent or application file contains at least one drawings executed in color. Copies of this patent or patent application publication with color drawing(s) will be provided by the U.S. Patent and Trademark Office upon request and payment of the necessary fee.

Drawings/diagrams, labeled and correlated with the description.

A) PCA was performed using expression values of a subset (47) of SAM identified differentially regulated miRNAs between normal brain tissue samples (n=7) and malignant astrocytoma tumor samples (n=39) as shown in Table 2. A scatter plot is generated using the first three principal components for each sample. The color of the samples is as indicated.

B, C, D) One-way hierarchical clustering of SAM identified grade specific miRNAs that differentiate GBM from AA (B), pGBM from sGBM (C) and progressive astroctyoma from de novo GBM (D). A dual color code was used with red and green indicating up and down-regulation, respectively.

A) One-way hierarchical clustering of PAM identified 24 miRNAs that discriminated GBM from AA. A dual color code was used with red and green indicating up- and down regulation, respectively.

B) PCA was performed using expression values of PAM identified 24 miRNAs as the most discriminatory between GBM and AA as shown in Table 6. A scatter plot is generated using the first three principal components for each sample (13 AA and 26 GBM tumor samples). The color of the samples is as indicated.

The detailed probabilities of 10-fold cross-validation for the 39 malignant astrocytoma samples based the expression values of PAM identified 24 miRNA are shown. For each sample, its probability as AA (orange color) and GBM (blue color) are shown and it was assigned by the PAM program as either AA or GBM based on which grade's probability is higher. The original histological grade of the samples is shown on the top. The threshold used for training is 2.3.

Table 1: Details of the samples used for microarray analysis.

Table 2: Differentially regulated miRNAs in malignant astrocytoma.

Table 3: Differentially regulated miRNAs between GBM and AA.

Table 4: Differentially regulated miRNAs between sGBM and pGBM.

Table 5: miRNAs differentially regulated between progressive pathway and de novo pathway Table 6: PAM identified 24 miRNA signature that differentiates GBM from AA Table 7: Prediction of GBM and AA with PAM using 24 miRNA expression signature.

DETAILED DESCRIPTION OF INVENTION

The present invention provides diagnostic kits for classifying different grades of glioma. This invention is used in the diagnosis of (1) Malignant Astrocytoma and Normal Brain sample, (2) Glioblastoma and Anaplastic Astrocytoma, (3) Secondary Glioblastoma and Primary Glioblastoma, (4) Progressive pathway and de novo pathway.

The invention is novel because currently the classification of grades of Glioma, types of GBMs is based on the observed histopathological characteristics of the tumor which is sometimes subjective and inconsistent. The invention provides diagnostic markers which can accurately classify different grades of glioma.

In order to obtain a histology independent miRNA expression signature to differentiate GBM from AA tumors, inventors have analyzed the expression of 756 miRNAs by microarray in 13 AA and 29 GBM tumor samples. In addition to identifying grade specific miRNAs, we were able to identify a 24 miRNA expression signature set that precisely differentiated GBM from AA with an accuracy rate of 95%.

Through microarray and real-time quantitative PCR, inventors found several differentially regulated miRNAs to be specific markers for distinguishing and diagnosing (1) Malignant Astrocytoma and Normal Brain sample, (2) Glioblastoma and Anaplastic astrocytoma, (3) Secondary Glioblastoma and Primary Glioblastoma, (4) Progressive pathway and de novo pathway, thus, to be able to administer appropriate treatment.

The present invention relates to a method of diagnosing (1) Malignant Astrocytoma and Normal Brain sample, (2) Glioblastoma and Anaplastic astrocytoma, (3) Secondary Glioblastoma and Primary Glioblastoma, (4) Progressive pathway and de novo pathway in human subject.

Glioma includes 1. Diffuse Oligodendroglioma (DO; WHO Gr. II), 2. Anaplastic. Oligodendroglioma (AO; WHO Gr. III), 3. Diffuse astrocytoma (DA; WHO Gr. II), 4. Anaplastic astrocytoma (AA; WHO Gr. III) and 5. Glioblastoma (GBM; WHO Gr. IV). GBMs are of two types: primary GBM (de novo type), which manifests in older patients (mean age: 55 yrs), as an aggressive, highly invasive tumor, usually without any evidence of prior clinical disease after a short clinical history of less than 3 months; Secondary GBM (progressive type) is usually seen in younger patients (mean age: 40 yrs) and develops more slowly by malignant progression from diffuse (WHO Grade II) or anaplastic astrocytoma (WHO Grade III).

The inventive method involves collecting or otherwise obtaining a sample of a bodily substance derived from the human subject, which sample contains human nucleic acid originating from the subject, and quantitatively determining therein the level of expression of the gene coding for specific miRNA. This includes detection by means of measuring of specific nucleic acid, such as miRNA.

The sample is preferably collected directly from the human subject's body. Preferred and convenient substances for sampling include cellular material from brain tissue. This includes normal brain tissue, brain tumor tissue.

In accordance with the inventive methods, the tissue sample preferably contains cells that express a plurality of miRNA species, which miRNA species are detectably distinct from one another. "Obtaining" and "collecting" the sample are used interchangeably herein and encompass sampling, resecting, removing from in situ, aspirating, receiving, gathering, and/or transporting the tissue sample or a concentrate, sediment, precipitate, supernatant, filtrate, aspirate, or other fraction of any of these. For example, conventional biopsy methods are useful for obtaining the tissue sample. These include percutaneous biopsy, laparoscopic biopsy, surgical resection, tissue scrapes and swabs, sampling via stents, catheters, endoscopes, needles, surgical resection, and other known means. For example, to obtain a sample from inside the skull of the human subject; typically, Magnetic Resonance Imaging (MRI)-guided stereotactic techniques are employed, but other methods can be used.

The sample is alternatively derived from cultured human cells, cell-free extracts, cell conditioned medium or other specimens indirectly derived from a subject's body, as well as from substances taken directly from a subject's body. Samples may be stored before detection methods are applied (for example nucleic acid amplification and/or analysis, or immunochemical detection) by well known storage means that will preserve nucleic acids in a detectable and/or analyzable condition, such as quick freezing, or a controlled freezing regime, in the presence of a cryoprotectant, for example, dimethyl sulfoxide (DMSO), trehalose, glycerol, or propanediol-sucrose. Samples may also be pooled before or after storage for purposes of amplifying the nucleic acids specific for the said genes for analysis and detection.

The sample is used immediately or optionally pre-treated by refrigerated or frozen storage overnight, by dilution, by phenol-chloroform extraction, or by other like means, to remove factors that may inhibit various amplification reactions. The level of expression in the sample for the said micro ribonucleic acid (miRNA) is then detected quantitatively. Polynucleotides specific for the said genes, including miRNA species, are determined by base sequence similarity or homology to known nucleotide sequences. Base sequence homology is determined by conducting a base sequence similarity search of a genomics data base, such as the GenBank database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data). (Altchul, et al., 1997; Zhang and Madden, 1997; Madden et al., 1996; Altschul et al., 1990).

Preferably, polynucleotide sequences specific to the said genes, including an mRNA sequence, is at least 5 to 30 contiguous nucleotides long, more preferably at least 6 to 15 contiguous nucleotides long, and most preferably at least 7 to 10 contiguous nucleotides long. mRNA specific to any of the said genes can be, but is not necessarily, an mRNA species containing a nucleotide sequence that encodes a functional version of the said genes or fragments thereof. Also included among mRNAs specific to the said genes are splice variants.

Quantitative detection of levels of miRNAs specific to the said genes of interest in accordance with the present invention is done by any known method that provides a quantitative determination of expression. A quantitative method can be absolute or relative. An absolute quantitation provides an absolute value for the amount or level of expression in comparison to a standard, which amount or level is typically a mole, mass, or activity value normalized in terms of a specified mass of protein, mass of nucleic acid, number or mass of cells, body weight, or the like. Additionally, the quantitative or absolute value is optionally normalized in terms of a specified time period, i.e., expression level as a rate. A relative detection method provides a unitless relative value for the amount or level of expression, for example, in terms of a ratio of expression in a given sample relative to a control, such as normal tissue or the expression of a selected "housekeeping" gene. The skilled artisan is aware of other examples of quantitative detection methods.

The quantitative detection of the expression level of miRNA species is accomplished by any of numerous methods of nucleic acid amplification (e.g., amplification of specific nucleic acid segments) in the form of RNA or cDNA, which RNA or cDNA amplification product is ultimately measured after amplification. The final amplification product of RNA or cDNA is measured by any conventional means, such as, but not limited to, densitometry, fluorescence detection, or any other suitable biochemical or physical assay system. Before amplification, it is preferable to extract or separate mRNA from genomic DNA in the sample and to amplify nucleic acids remaining in that fraction of the sample separated from the DNA, to avoid false positives that are caused by amplification of contaminating genomic DNA in the original specimen.

The foregoing descriptions of the methods of the present invention are only illustrative and by no means exhaustive. When these features of the present invention are employed, diagnostic and treatment decisions can be more appropriately optimized for the individual glioma patient.

Differential Expression of miRNAs Between Malignant Astrocytomas and Normal Brains:

Inventors performed a systematic miRNA expression profiling of 756 human miRNAs on 39 glioma samples, samples (26 glioblastoma/GBM-13 pGBMs and 13 sGBMs; 13 anaplastic astrocytoma/AA) and 7 normal brain samples (Table 1).

TABLE 1

Details of the samples used for microarray analysis

| No. | Sample ID | Histological grade | Classification as per miRNA signature |
|---|---|---|---|
| 1 | Normal1 | NORMAL | NORMAL |
| 2 | Normal2 | NORMAL | NORMAL |
| 3 | Normal3 | NORMAL | NORMAL |
| 4 | Normal5 | NORMAL | NORMAL |
| 5 | Normal6 | NORMAL | NORMAL |
| 6 | Normal7 | NORMAL | NORMAL |
| 7 | Normal8 | NORMAL | NORMAL |
| 8 | CN42 | AA III | AA III |
| 9 | CN43 | AA III | AA III |
| 10 | CN44 | AA III | AA III |
| 11 | CN47 | AA III | AA III |
| 12 | CN48 | AA III | AA III |
| 13 | CN49 | AA III | AA III |
| 14 | CN50 | AA III | GBM |
| 15 | CN51 | AA III | GBM |
| 16 | CN52 | AA III | AA III |
| 17 | CN55 | AA III | AA III |
| 18 | CN56 | AA III | AA III |
| 19 | CN57 | AA III | AA III |
| 20 | CN62 | AA III | AA III |
| 21 | CN1 | pGBM IV | GBM |
| 22 | CN2 | pGBM IV | GBM |

TABLE 1-continued

Details of the samples used for microarray analysis

| No. | Sample ID | Histological grade | Classification as per miRNA signature |
|---|---|---|---|
| 23 | CN3 | pGBM IV | GBM |
| 24 | CN4 | pGBM IV | GBM |
| 25 | CN5 | pGBM IV | GBM |
| 26 | CN6 | pGBM IV | GBM |
| 27 | CN7 | pGBM IV | GBM |
| 28 | CN9 | pGBM IV | GBM |
| 29 | CN11 | pGBM IV | GBM |
| 30 | CN12 | pGBM IV | GBM |
| 31 | CN13 | pGBM IV | GBM |
| 32 | CN29 | pGBM IV | GBM |
| 33 | CN39 | pGBM IV | GBM |
| 34 | CN17 | sGBM IV | GBM |
| 35 | CN18 | sGBM IV | GBM |
| 36 | CN22 | sGBM IV | GBM |
| 37 | CN23 | sGBM IV | GBM |
| 38 | CN25 | sGBM IV | GBM |
| 39 | CN26 | sGBM IV | GBM |
| 40 | CN31 | sGBM IV | AA III |
| 41 | CN32 | sGBM IV | GBM |
| 42 | CN33 | sGBM IV | GBM |
| 43 | CN34 | sGBM IV | GBM |
| 44 | CN35 | sGBM IV | GBM |
| 45 | CN36 | sGBM IV | AA III |
| 46 | CN37 | sGBM IV | GBM |

The data obtained from image analysis was filtered, normalized and log 2 transformed before using for further analysis. To identify the significantly differentially regulated miRNAs between normal and astrocytoma samples, we analyzed a total of 287 miRNAs through Significance Analysis of Microarrays (SAM) using the two-class option (16). At a false discovery rate (FDR) of 0.0%, we found 53 miRNAs to be up regulated and 24 miRNAs down regulated in malignant astrocytomas in comparison to normal brain samples. For visual appreciation miRNA regulation, the data obtained from SAM was subjected to a supervised, one-way, average-linkage hierarchical cluster analysis with Euclidean distance as similarity metric, using the TMev software (FIG. S1; Table 2).

TABLE 2

Differentially regulated miRNAs in malignant astrocytoma

- miRNAs up regulated in malignant astrocytoma compared to normals

| No | Annotation | Median of normals$ (log2) | Median of astrocytoma$ (log2) | Difference (log2) | Fold change |
|---|---|---|---|---|---|
| 1 | hsa-miR-92b | 0.00 | 2.31 | 2.31 | 4.97 |
| 2 | hsa-miR-25 | −0.01 | 2.04 | 2.05 | 4.13 |
| 3 | hsa-miR-195 | 0.03 | 2.05 | 2.02 | 4.06 |
| 4 | hsa-miR-193a-3p | −0.18 | 1.81 | 1.99 | 3.96 |
| 5 | hsa-miR-106b | 0.14 | 2.11 | 1.97 | 3.92 |
| 6 | hsa-miR-130a | −0.01 | 1.90 | 1.91 | 3.76 |
| 7 | hsa-miR-10a | 0.02 | 1.85 | 1.83 | 3.55 |
| 8 | hsa-miR-23a | 0.07 | 1.83 | 1.76 | 3.39 |
| 9 | hsa-miR-19b | −0.01 | 1.75 | 1.76 | 3.39 |
| 10 | hsa-miR-93 | 0.13 | 1.89 | 1.76 | 3.38 |
| 11 | hsa-miR-105 | 0.11 | 1.76 | 1.65 | 3.13 |
| 12 | hsa-miR-19a | 0.00 | 1.62 | 1.63 | 3.08 |
| 13 | hsa-miR-497 | 0.10 | 1.71 | 1.61 | 3.06 |
| 14 | hsa-miR-15b | −0.05 | 1.51 | 1.56 | 2.96 |
| 15 | hsa-miR-142-3p | 0.20 | 1.75 | 1.55 | 2.93 |
| 16 | hsa-miR-20b | 0.08 | 1.60 | 1.52 | 2.87 |
| 17 | hsa-miR-142-5p | 0.06 | 1.56 | 1.50 | 2.84 |
| 18 | hsa-miR-182 | 0.10 | 1.59 | 1.49 | 2.80 |
| 19 | hsa-miR-542-5p | −0.04 | 1.35 | 1.39 | 2.62 |
| 20 | hsa-miR-199a-3p/ hsa-miR-199b-3p | 0.19 | 1.52 | 1.33 | 2.51 |

TABLE 2-continued

Differentially regulated miRNAs in malignant astrocytoma

| 21 | hsa-miR-16 | 0.08 | 1.34 | 1.27 | 2.41 |
|----|------------|------|------|------|------|
| 22 | hsa-miR-106a | 0.21 | 1.48 | 1.26 | 2.40 |
| 23 | hsa-miR-130b | −0.13 | 1.09 | 1.23 | 2.34 |
| 24 | hsa-miR-15a | 0.38 | 1.59 | 1.21 | 2.31 |
| 25 | hsa-miR-155 | 0.19 | 1.38 | 1.19 | 2.28 |
| 26 | hsa-miR-505 | −0.12 | 1.07 | 1.18 | 2.27 |
| 27 | hsa-miR-32 | 0.00 | 1.16 | 1.16 | 2.24 |
| 28 | hsa-miR-17 | 0.24 | 1.39 | 1.15 | 2.22 |
| 29 | hsa-miR-144 | 0.26 | 1.41 | 1.15 | 2.21 |
| 30 | hsa-miR-374b | 0.15 | 1.29 | 1.14 | 2.21 |
| 31 | hsa-miR-99a | 0.12 | 1.26 | 1.14 | 2.21 |
| 32 | hsa-miR-146a | 0.04 | 1.18 | 1.13 | 2.20 |
| 33 | hsa-miR-152 | 0.00 | 1.12 | 1.13 | 2.18 |
| 34 | hsa-miR-320a | −0.02 | 1.10 | 1.12 | 2.18 |
| 35 | hsa-miR-374a | 0.40 | 1.52 | 1.12 | 2.17 |
| 36 | hsa-miR-450a | 0.02 | 1.12 | 1.09 | 2.14 |
| 37 | hsa-miR-362-3p | 0.00 | 1.07 | 1.07 | 2.10 |
| 38 | hsa-miR-96 | −0.01 | 1.05 | 1.06 | 2.08 |
| 39 | hsa-miR-9 | 0.48 | 1.50 | 1.02 | 2.03 |
| 40 | hsa-miR-424 | 0.11 | 1.13 | 1.02 | 2.03 |
| 41 | hsa-miR-550 | −0.03 | 0.97 | 1.01 | 2.01 |
| 42 | hsa-miR-532-5p | −0.09 | 0.91 | 1.00 | 2.00 |
| 43 | hsa-miR-215 | −0.02 | 0.98 | 1.00 | 2.00 |
| 44 | hsa-miR-92a | 0.08 | 1.06 | 0.98 | 1.97 |
| 45 | hsa-miR-106b* | −0.06 | 0.92 | 0.98 | 1.97 |
| 46 | hsa-miR-660 | −0.01 | 0.93 | 0.94 | 1.92 |
| 47 | hsa-miR-20b* | −0.05 | 0.85 | 0.91 | 1.88 |
| 48 | hsa-miR-17* | −0.15 | 0.67 | 0.82 | 1.76 |
| 49 | hsa-miR-199b-5p | 0.12 | 0.89 | 0.78 | 1.71 |
| 50 | hsa-miR-135b | 0.32 | 1.02 | 0.71 | 1.63 |
| 51 | hsa-miR-181a-2* | −0.01 | 0.66 | 0.67 | 1.59 |
| 52 | hsa-miRPlus-A1083 | −0.02 | 0.62 | 0.64 | 1.56 |
| 53 | hsa-miR-122* | 0.04 | 0.50 | 0.46 | 1.38 |

II-miRNAs down regulated in malignant astrocytoma compared to normals

| No. | Annotation | Median of normals | Median of astrocytoma | Difference | Fold change |
|-----|------------|-------------------|------------------------|------------|-------------|
| 1 | hsa-miR-129-3p | 0.00 | −3.36 | −3.36 | 10.29 |
| 2 | hsa-miR-638 | 0.48 | −1.64 | −2.12 | 4.35 |
| 3 | hsa-miRPlus-A1056 | 0.33 | −1.77 | −2.10 | 4.29 |
| 4 | hsa-miR-637 | 0.31 | −1.77 | −2.08 | 4.22 |
| 5 | hsa-miR-338-3p | 0.10 | −1.88 | −1.98 | 3.95 |
| 6 | hsa-miR-323-3p | 0.14 | −1.79 | −1.93 | 3.80 |
| 7 | hsa-miRPlus-D1036 | 0.02 | −1.84 | −1.86 | 3.64 |
| 8 | hsa-miR-219-2-3p | −0.11 | −1.97 | −1.86 | 3.63 |
| 9 | hsa-miR-132 | 0.27 | −1.45 | −1.72 | 3.29 |
| 10 | hsa-miR-1908 | 0.13 | −1.57 | −1.70 | 3.26 |
| 11 | hsa-miR-129-5p | −0.06 | −1.76 | −1.70 | 3.25 |
| 12 | hsa-miR-219-5p | −0.43 | −2.12 | −1.69 | 3.23 |
| 13 | hsa-miR-483-5p | 0.01 | −1.65 | −1.66 | 3.15 |
| 14 | hsa-miR-329 | 0.03 | −1.61 | −1.64 | 3.12 |
| 15 | hsa-miRPlus-A1027 | 0.17 | −1.39 | −1.56 | 2.95 |
| 16 | hsa-miR-198 | 0.03 | −1.49 | −1.52 | 2.88 |
| 17 | hsa-miR-665 | −0.02 | −1.52 | −1.50 | 2.83 |
| 18 | hsa-miR-628-3p | 0.13 | −1.30 | −1.43 | 2.69 |
| 19 | hsa-miR-338-5p | −0.11 | −1.24 | −1.13 | 2.18 |
| 20 | hsa-miR-765 | −0.05 | −1.16 | −1.11 | 2.16 |
| 21 | hsa-miR-432 | 0.04 | −0.98 | −1.02 | 2.03 |
| 22 | hsa-miR-498 | 0.06 | −0.80 | −0.85 | 1.81 |
| 23 | hsa-miR-485-3p | 0.03 | −0.81 | −0.83 | 1.78 |
| 24 | hsa-miR-584 | −0.08 | −0.56 | −0.47 | 1.39 |

Figure 1:
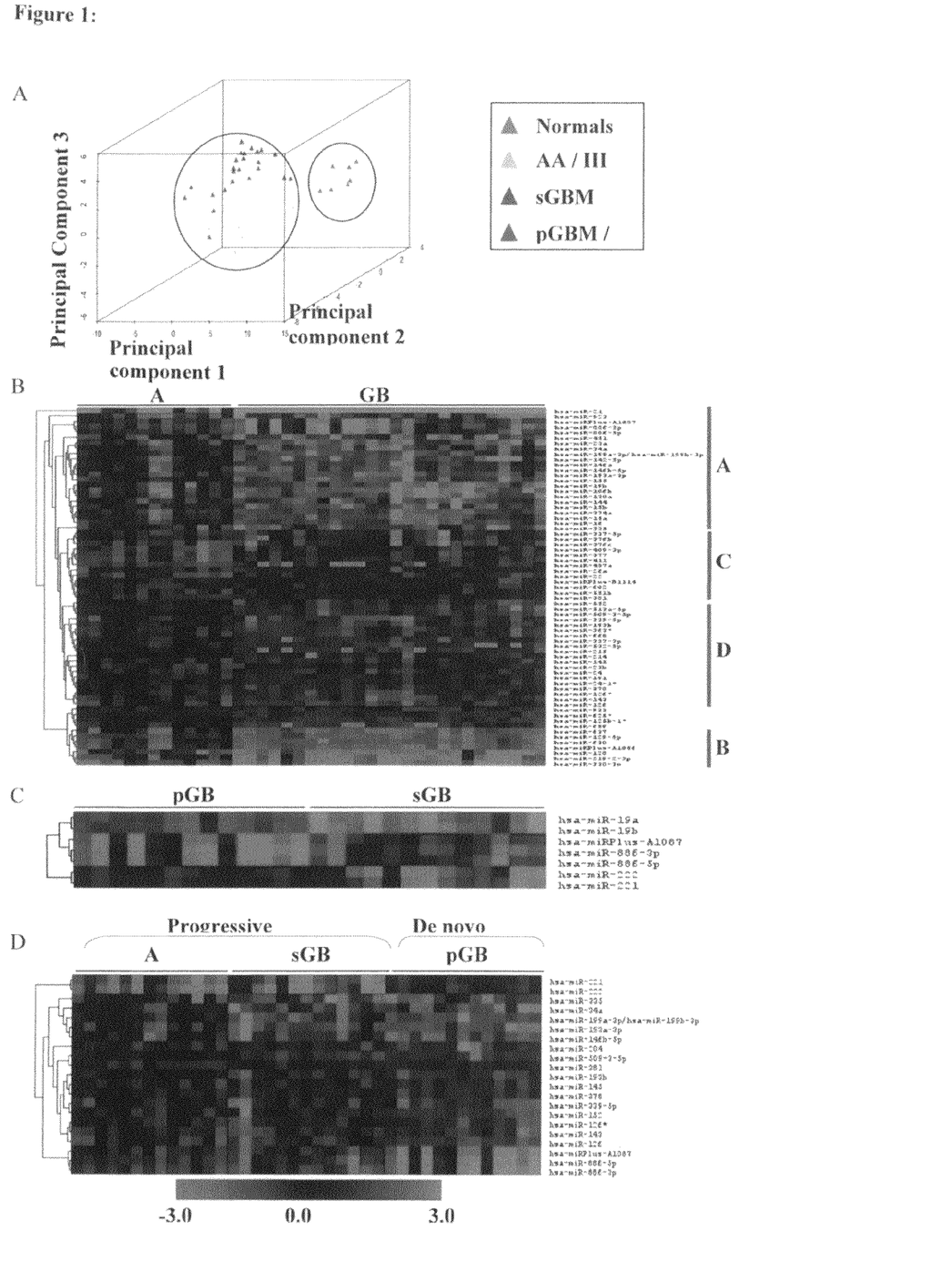
FIG. 1. Identification of tumor grade specific miRNA.

$median log2 ratio of 7 normal samples and 39 astrocytoma (13 AA and 26 GBM) samples are shown We further performed Principal Component Analysis (PCA) using a subset of SAM identified significant miRNAs. Malignant astrocytoma samples (blue, purple and orange triangles) and normal brain (green triangle) samples separated clearly into two major clusters (FIG. 1A). Further, within malignant astrocytoma, GBMs (blue and, purple triangles) and AAs (orange triangles) formed two sub clusters (Upper vs. Lower sections respectively).

Differentially Regulated miRNAs Between Malignant Astrocytoma Grades:

We identified through SAM (FDR 0.0%) that a total of 67 miRNAs to be differentially regulated between AA and GBM grades (FIG. 1B; Table 3).

TABLE 3

Differentially regulated miRNAs between GBM and AA.

I- miRNAs up regulated in GBM compared to AA

| No. | Annotation | Median of AA$ (log2) | Median of GBM$ (log2) | Difference (log2) | Fold change |
|-----|------------|----------------------|------------------------|--------------------|-------------|
| 1 | hsa-miR-532-5p | 0.40 | 0.99 | 0.60 | 1.51 |
| 2 | hsa-miR-24-1* | 0.09 | 0.75 | 0.66 | 1.58 |
| 3 | hsa-miR-144 | 0.68 | 1.75 | 1.07 | 2.10 |
| 4 | hsa-miRPlus-B1114 | −0.24 | 0.35 | 0.59 | 1.51 |
| 5 | hsa-miR-19b | 0.79 | 2.02 | 1.23 | 2.35 |
| 6 | hsa-miR-602 | −0.32 | 0.26 | 0.59 | 1.50 |
| 7 | hsa-miR-26a | 0.04 | 0.52 | 0.48 | 1.39 |
| 8 | hsa-miR-374a | 0.79 | 1.75 | 0.96 | 1.95 |
| 9 | hsa-miR-23a | 1.19 | 2.07 | 0.88 | 1.84 |
| 10 | hsa-miR-214 | 0.13 | 0.57 | 0.44 | 1.36 |
| 11 | hsa-miR-337-3p | 0.18 | 0.97 | 0.79 | 1.73 |
| 12 | hsa-miR-339-5p | 0.24 | 1.19 | 0.95 | 1.93 |
| 13 | hsa-miR-363* | 0.16 | 1.11 | 0.96 | 1.94 |
| 14 | hsa-miR-193b | 0.06 | 1.09 | 1.02 | 2.03 |
| 15 | hsa-miR-145 | −0.33 | 0.62 | 0.95 | 1.93 |
| 16 | hsa-miR-106b | 1.09 | 2.32 | 1.23 | 2.34 |
| 17 | hsa-miR-23b | −0.60 | 0.30 | 0.89 | 1.86 |
| 18 | hsa-miR-886-3p | −0.71 | 1.22 | 1.93 | 3.82 |
| 19 | hsa-miRPlus-A1087 | −0.21 | 1.21 | 1.42 | 2.68 |
| 20 | hsa-miR-130a | 0.79 | 2.01 | 1.22 | 2.34 |
| 21 | hsa-miR-126* | 0.15 | 0.92 | 0.77 | 1.70 |
| 22 | hsa-miR-377 | −0.99 | 0.10 | 1.08 | 2.12 |
| 23 | hsa-miR-15a | 0.68 | 1.75 | 1.07 | 2.09 |
| 24 | hsa-miR-146a | 0.34 | 1.38 | 1.04 | 2.06 |
| 25 | hsa-miR-409-3p | −1.27 | −0.10 | 1.17 | 2.25 |
| 26 | hsa-miR-668 | 0.26 | 1.04 | 0.78 | 1.71 |
| 27 | hsa-miR-411 | −1.15 | −0.19 | 0.96 | 1.95 |
| 28 | hsa-miR-551b | −0.57 | 0.10 | 0.67 | 1.59 |
| 29 | hsa-miR-487a | −1.14 | −0.16 | 0.97 | 1.96 |
| 30 | hsa-miR-886-5p | −0.60 | 1.32 | 1.91 | 3.77 |
| 31 | hsa-miR-337-5p | −0.38 | 0.86 | 1.24 | 2.37 |
| 32 | hsa-miR-376b | −0.12 | 0.75 | 0.87 | 1.83 |
| 33 | hsa-miR-923 | −0.67 | 0.72 | 1.39 | 2.62 |
| 34 | hsa-miR-34a | 0.25 | 1.69 | 1.45 | 2.73 |
| 35 | hsa-miR-451 | 0.22 | 1.82 | 1.61 | 3.04 |
| 36 | hsa-miR-191 | −0.09 | 0.70 | 0.80 | 1.74 |
| 37 | hsa-miR-199a-3p/ hsa miR-199b-3p | 0.47 | 1.85 | 1.38 | 2.60 |
| 38 | hsa-miR-146b-5p | 0.20 | 1.49 | 1.30 | 2.46 |
| 39 | hsa-miR-15b | 0.82 | 1.90 | 1.08 | 2.12 |
| 40 | hsa-miR-376c | −0.83 | 0.98 | 1.80 | 3.49 |
| 41 | hsa-miR-21 | 2.47 | 4.81 | 2.34 | 5.05 |
| 42 | hsa-miR-142-5p | 0.22 | 1.71 | 1.49 | 2.81 |
| 43 | hsa-miR-24 | −0.47 | 0.67 | 1.14 | 2.21 |
| 44 | hsa-miR-193a-3p | 0.34 | 1.90 | 1.56 | 2.95 |
| 45 | hsa-miR-22 | −1.03 | 0.25 | 1.28 | 2.42 |
| 46 | hsa-miR-378 | 0.01 | 0.86 | 0.85 | 1.81 |
| 47 | hsa-miR-552 | −0.12 | 1.11 | 1.22 | 2.33 |
| 48 | hsa-miR-215 | 0.47 | 1.13 | 0.66 | 1.58 |
| 49 | hsa-miR-155 | 0.46 | 1.81 | 1.35 | 2.54 |
| 50 | hsa-miR-513a-5p | 0.13 | 1.18 | 1.05 | 2.08 |
| 51 | hsa-miR-16 | 0.14 | 1.64 | 1.50 | 2.83 |
| 52 | hsa-miR-143 | −0.31 | 1.17 | 1.48 | 2.79 |
| 53 | hsa-miR-335 | 0.11 | 1.57 | 1.46 | 2.76 |
| 54 | hsa-miR-509-3-5p | −0.07 | 1.14 | 1.21 | 2.31 |
| 55 | hsa-miR-381 | −0.71 | 0.49 | 1.19 | 2.29 |
| 56 | hsa-miR-126 | −0.27 | 1.31 | 1.58 | 3.00 |

II- miRNAs down regulated in GBM compared to AA

| No. | Annotation | Median of AA | Median of GBM | Difference | Fold change |
|-----|------------|--------------|----------------|------------|-------------|
| 1 | hsa-miR-129-5p | −0.86 | −1.87 | −1.01 | 2.01 |
| 2 | hsa-miR-219-2-3p | −0.28 | −2.64 | −2.36 | 5.13 |
| 3 | hsa-miR-638 | −0.50 | −1.68 | −1.18 | 2.26 |
| 4 | hsa-miR-125b-1* | −0.31 | −0.77 | −0.47 | 1.38 |

TABLE 3-continued

Differentially regulated miRNAs between GBM and AA.

| 5 | hsa-miR-625* | −0.01 | −0.50 | −0.49 | 1.40 |
| 6 | hsa-miR-128 | −0.78 | −2.39 | −1.61 | 3.05 |
| 7 | hsa-miR-637 | −0.65 | −1.88 | −1.23 | 2.35 |
| 8 | hsa-miR-933 | 0.22 | −0.65 | −0.87 | 1.83 |
| 9 | hsa-miRPlus-A1056 | −0.73 | −1.87 | −1.14 | 2.21 |
| 10 | hsa-miR-659 | −0.02 | −0.84 | −0.82 | 1.76 |
| 11 | hsa-miR-338-3p | −1.37 | −2.38 | −1.00 | 2.00 |

$median log2 ratio of 13 AA samples and 26 GBM samples are shown.

Among these 67 differentially regulated miRNAs, there were four sub clusters with different patterns of expression. The cluster A and B consists of miRNAs which are up regulated and down regulated in both AA and GBM with up regulation and down regulation reaching substantially high levels in GBM in comparison to AA. In the cluster C and D the expression levels of these miRNAs in AA are either less than normal (cluster C) or similar to normal (cluster D) while they are highly up regulated in GBM samples. On comparison of sGBM (n=13) with pGBM (n=13), we found 7 miRNAs to be differentially regulated significantly at a FDR of 0.0% (FIG. 1C; Table 4).

TABLE 4

Differentially regulated miRNAs between sGBM and pGBM.

| No. | Annotation | Median of sGBM$ (log2) | Median of pGBM$ (log2) | Difference (log2) | Fold change |
|---|---|---|---|---|---|
| | I- miRNAs up regulated in sGBM compared to pGBM | | | | |
| 1 | hsa-miR-19a | 2.19 | 1.58 | 0.61 | 1.53 |
| 2 | hsa-miR-19b | 2.57 | 1.57 | 1.00 | 2.00 |
| | II- miRNAs down regulated in sGBM compared to pGBM | | | | |
| 1 | hsa-miR-886-3p | 0.21 | 2.84 | −2.63 | 6.19 |
| 2 | hsa-miRPlus-A1087 | 0.57 | 2.58 | −2.00 | 4.01 |
| 3 | hsa-miR-886-5p | 0.66 | 2.83 | −2.17 | 4.52 |
| 4 | hsa-miR-222 | −1.92 | −0.21 | −1.71 | 3.27 |
| 5 | hsa-miR-221 | −0.94 | 0.15 | −1.09 | 2.13 |

$median log2 ratio of 13 sGBM samples and 13 pGBM samples are shown.

When progressive astrocytoma samples (n=26; 13 AA and 13 sGBM) were compared against pGBM (de novo GBM; n=13 pGBM), we found 21 miRNAs to be differentially regulated (FIG. 1D; Table 5).

TABLE 5 miRNAs differentially regulated between progressive pathway and de novo pathway

| No. | Annotation | Median of progressive type$ (log2) | Median of de novo type$ (log2) | Difference (log2) | Fold change |
|---|---|---|---|---|---|
| 1 | hsa-miR-886-3p | −0.45 | 2.84 | 3.29 | 9.77 |
| 2 | hsa-miR-886-5p | −0.28 | 2.83 | 3.11 | 8.66 |
| 3 | hsa-miRPlus-A1087 | 0.04 | 2.58 | 2.54 | 5.82 |
| 4 | hsa-miR-222 | −1.96 | −0.21 | 1.75 | 3.36 |
| 5 | hsa-miR-221 | −1.47 | 0.15 | 1.62 | 3.07 |
| 6 | hsa-miR-146b-5p | 0.83 | 2.01 | 1.18 | 2.27 |
| 7 | hsa-miR-126 | 0.29 | 1.43 | 1.13 | 2.19 |
| 8 | hsa-miR-34a | 0.81 | 1.83 | 1.01 | 2.02 |
| 9 | hsa-miR-204 | −0.10 | 0.87 | 0.97 | 1.96 |
| 10 | hsa-miR-335 | 0.75 | 1.67 | 0.91 | 1.88 |
| 11 | hsa-miR-152 | 0.54 | 1.35 | 0.82 | 1.76 |
| 12 | hsa-miR-199a-3p/ hsa-miR-199b-3p | 1.05 | 1.86 | 0.81 | 1.76 |
| 13 | hsa-miR-193b | 0.45 | 1.23 | 0.78 | 1.72 |
| 14 | hsa-miR-381 | −0.22 | 0.51 | 0.74 | 1.66 |
| 15 | hsa-miR-143 | 0.52 | 1.17 | 0.65 | 1.57 |
| 16 | hsa-miR-509-3-5p | 0.56 | 1.11 | 0.55 | 1.46 |
| 17 | hsa-miR-339-5p | 0.76 | 1.28 | 0.53 | 1.44 |
| 18 | hsa-miR-193a-3p | 1.42 | 1.92 | 0.49 | 1.41 |
| 19 | hsa-miR-126* | 0.57 | 1.03 | 0.47 | 1.38 |
| 20 | hsa-miR-145 | 0.34 | 0.73 | 0.39 | 1.31 |
| 21 | hsa-miR-378 | 0.52 | 0.89 | 0.37 | 1.29 |

$median log2 ratio of 26 progressive astrocytoma (13 AA and 13 sGBM) samples and 13 pGBM samples are shown.

Figure 2:
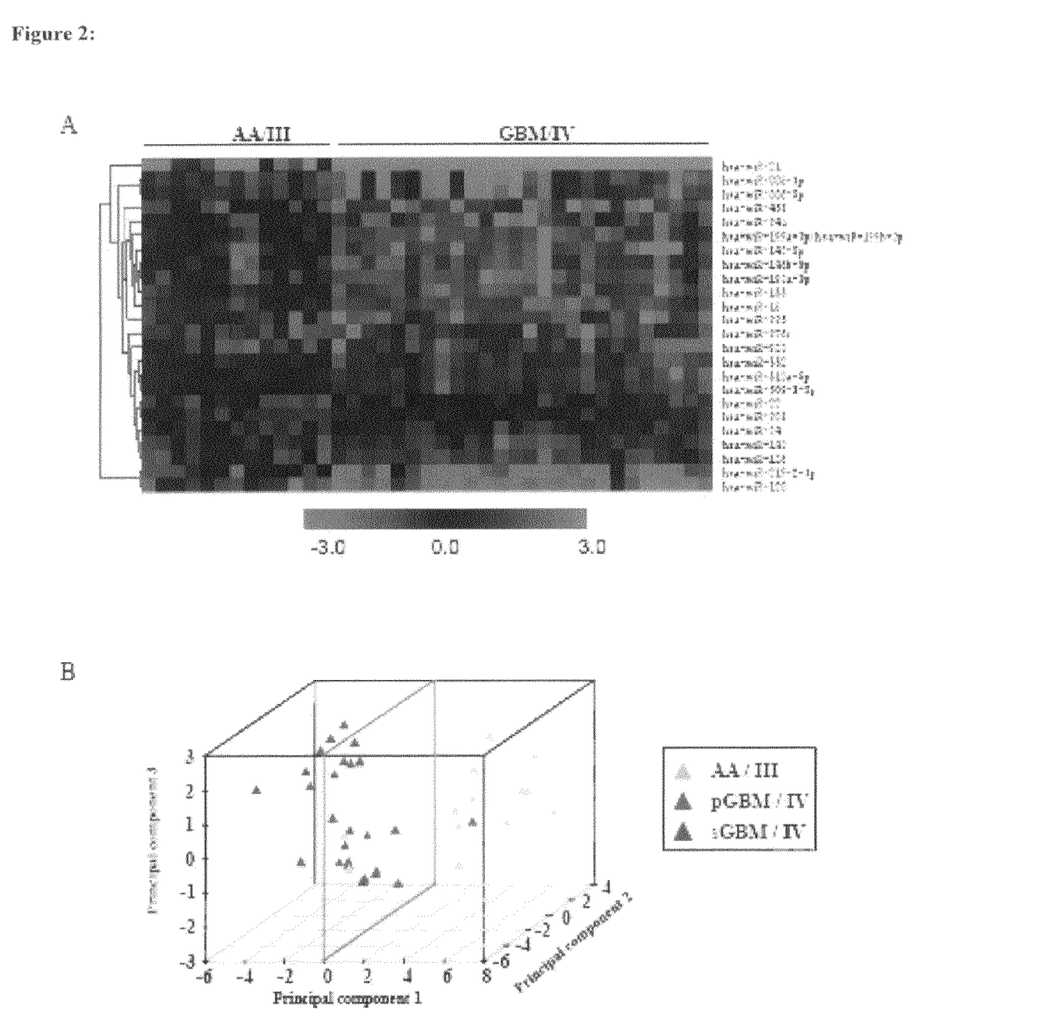
FIG. 2. Details of PAM identified 24 miRNA expression signature.

24 miRNA Expression Signature Differentiates GBM from AA Accurately:

We identified a 24 miRNA expression signature using Prediction Analysis of Microarray (PAM) to determine the minimal number of miRNAs to distinguish GBM and AA, and found 24 miRNA expression signature to be most discriminatory between GBM and AA cases (FIG. 2A and Table 6).

TABLE 6

PAM identified 24 miRNA signature that differentiates GBM from AA

| No | Annotation | Median of AA$ (log2) | Median of GBM$ (log2) | p value * | AA score# | GBM score# | Genomic location | Host gene |
|---|---|---|---|---|---|---|---|---|
| 1 | hsa-miR-126 | −0.27 | 1.31 | <0.0001 | −0.33 | 0.17 | Intragenic | EGFL-7 |
| 2 | hsa-miR-21 | 2.47 | 4.81 | 0.0008 | −0.14 | 0.07 | Intergenic | — |
| 3 | hsa-miR-146b-5p | 0.20 | 1.49 | 0.0003 | −0.03 | 0.02 | Intergenic | — |
| 4 | hsa-miR-155 | 0.46 | 1.81 | <0.0001 | −0.08 | 0.04 | Intragenic | AP000223.5 |
| 5 | hsa-miR-16 | 0.14 | 1.64 | <0.0001 | −0.10 | 0.05 | Intragenic | DLEU1 |
| 6 | hsa-miR-193a-3p | 0.34 | 1.90 | 0.002 | −0.08 | 0.04 | Intergenic | — |
| 7 | hsa-miR-199a-3p/ hsa-miR-199b-3p | 0.47 | 1.85 | <0.0001 | −0.02 | 0.01 | Intragenic | DNM2 |
| 8 | hsa-miR-22 | −1.03 | 0.25 | 0.0001 | −0.05 | 0.02 | Intragenic | C17ORF19 |
| 9 | hsa-miR-335 | 0.11 | 1.57 | <0.0001 | −0.26 | 0.13 | Intragenic | MEST |
| 10 | hsa-miR-143 | −0.31 | 1.17 | <0.0001 | −0.17 | 0.09 | Intergenic | — |
| 11 | hsa-miR-381 | −0.71 | 0.49 | <0.0001 | −0.13 | 0.06 | Intergenic | — |
| 12 | hsa-miR-24 | −0.47 | 0.67 | 0.0003 | 0.00 | 0.00 | Intragenic | C9orf3 |
| 13 | hsa-miR-552 | −0.12 | 1.11 | <0.0001 | −0.03 | 0.02 | Intergenic | — |
| 14 | hsa-miR-886-5p | −0.60 | 1.32 | 0.001 | −0.05 | 0.03 | Intergenic | — |

TABLE 6-continued

PAM identified 24 miRNA signature that differentiates GBM from AA

| No | Annotation | Median of AA$ (log2) | Median of GBM$ (log2) | p value * | AA score# | GBM score# | Genomic location | Host gene |
|---|---|---|---|---|---|---|---|---|
| 15 | hsa-miR-142-5p | 0.22 | 1.71 | 0.0002 | −0.07 | 0.04 | Intergenic | — |
| 16 | hsa-miR-34a | 0.25 | 1.69 | 0.0004 | −0.01 | 0.00 | Intergenic | — |
| 17 | hsa-miR-128 | −0.78 | −2.39 | 0.0002 | 0.03 | −0.02 | Intragenic | R3HDM1 |
| 18 | hsa-miR-923 | −0.67 | 0.72 | 0.0007 | −0.04 | 0.02 | Dead entry miRbase | — |
| 19 | hsa-miR-513a-5p | 0.13 | 1.18 | <0.0001 | −0.05 | 0.03 | Intergenic | — |
| 20 | hsa-miR-509-3-5p | −0.07 | 1.14 | <0.0001 | −0.13 | 0.06 | Intergenic | — |
| 21 | hsa-miR-376c | −0.83 | 0.98 | 0.0003 | −0.09 | 0.04 | Intergenic | — |
| 22 | hsa-miR-886-3p | −0.71 | 1.22 | 0.0023 | −0.01 | 0.01 | Intergenic | — |
| 23 | hsa-miR-219-2-3p | −0.28 | −2.64 | 0.0003 | 0.12 | −0.06 | Intergenic | — |
| 24 | hsa-miR-451 | 0.22 | 1.82 | 0.0023 | −0.03 | 0.01 | Intergenic | — |

$median log2 ratio of 13 AA samples and 26 GBM samples are shown
* p value was calculated by Mann Whitney-Non-parametric t test
Score is a measure of standardized centroid for each class.

Figure 3:
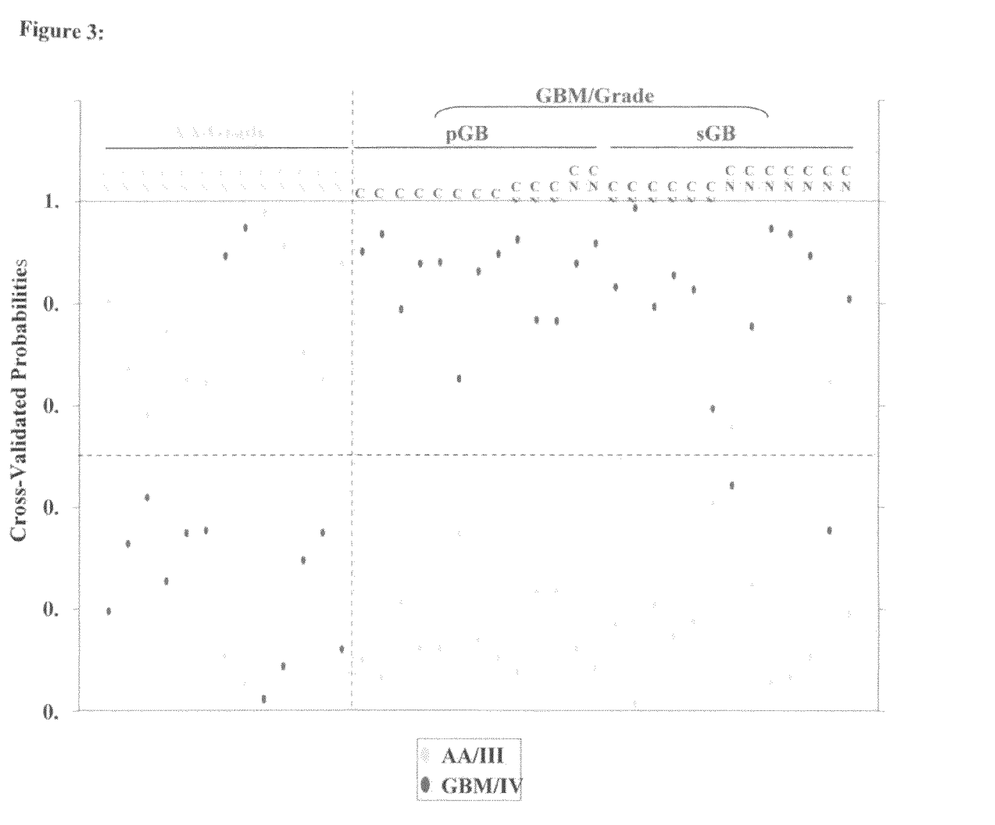
FIG. 3. The detailed cross-validated probabilities for AA and GBM tumor samples.

Upon PCA analysis of the 24 miRNA expression signature, most samples that belong to AA (orange triangles) and GBM (blue and purple triangles) formed two distinct groups (FIG. 2B). However, we found few samples that are discordant from the original histopathological grading, which might reflect inaccuracy in histopathological grading. Prediction accuracy estimation by 10-fold cross-validation using PAM (FIG. 3) revealed that among 13 AA samples, 11 samples were predicted as AA (cross-validated probability more than 0.5), while two samples (CN50 and CN51) were predicted as GBM with an error rate of 0.15. Similarly, among 26 GBM samples used, PAM predicted 24 samples correctly as GBM while two samples (CN31 and CN36) as AA with an error rate of 0.078. Thus the 24 miRNA expression signature can discriminate GBMs from AAs with an overall diagnostic accuracy of 89.7% (FIG. 3; Table 7). The sensitivity for AA is 84.6%, whereas for GBM, it is 92.3%; the specificity for AA is 92.3%, whereas for GBM, it is 84.6% (Table 7).

TABLE 7

Prediction of GBM and AA with PAM using 24 miRNA expression signature

| Grading | Overall accuracy[a] | Sensitivity[b] | Specificity[c] |
|---|---|---|---|
| Initial grading | 89.70% | AA: 84.6% (11/13) GBM: 92.3% (24/26) | AA: 92.3% (24/26) GBM: 84.6% (11/13) |
| Revised grading | 94.80% | AA: 92.3% (12/13) GBM: 96.2% (25/26) | AA: 96.2% (25/26) GBM: 92.3% (12/13) |

[a]Prediction accuracy was determined by 10-fold cross-validation on the 39 malignant astrocytoma samples consisting of 13 AA/III and 26 GBM/IV samples. Accuracy = (the number of samples predicted correctly)/(total number of samples analyzed)
[b]Sensitivity = (the number of positive samples predicted)/(the number of true positives).
[c]Specificity = (the number of negative samples predicted)/(the number of true negatives).

The four samples which were classified to different grades by PAM belonged to the progressive pathway (C50 and CN51=AA; CN31 and CN36=sGBM). In view of inherent sampling problems (mainly due to tumor location in the brain) and inadequate sample size available for histological evaluation, there exists a very high possibility of error in grading. Hence, we re-examined the histology of these four discordant cases after processing any additional material that we had in the laboratory. Interestingly, we found that among two sGBM samples, one (CN31) revealed focal areas of oligodendroglial component and hence this tumor was reclassified as a mixed anaplastic oligoastrocytoma (WHO grade III). Similarly, among two AA samples, histology review in one sample (CN50) after processing additional tumor bits revealed the presence of focal areas of necrosis and hence was reclassified as sGBM. Thus out of four samples in question as per miRNA expression signature, two samples were actually misclassified originally thereby increasing the overall diagnostic accuracy to 94.8% (Table 7). The sensitivity for AA is 92.3%, whereas for GBM, it is 96.2%; the specificity for AA is 96.2%, whereas for GBM, it is 92.3% (Table 7). However, the 24 miRNA expression signature identified all pGBM samples correctly thus with an accuracy of 100% for pGBM diagnosis.

The following examples are given by way of illustration of the present invention and therefore should not be constructed to limit the scope of the present invention.

Example 1

Tissue Collection

Tumor samples were collected from patients who were operated at National Institute of Mental Health and Neurosciences and Sri Satya Sai Institute of Higher Medical Sciences, Bangalore, India. A portion of the non-dominant anterior temporal cortex resected during surgery for intractable epilepsy served as normal control brain sample. A total of 73 samples of malignant astrocytoma and control brain tissue were used in this study. For microarray hybridization, a set of 39 samples of malignant astrocytoma comprising 13 AA, 13 sGBM and 13 pGBM tissues and 7 controls were used. For subsequent real time RT-PCR validation of selected miRNAs, we used an independent set of 24 samples of GBM and 3 controls. Tissues were bisected, and one half was snap-frozen in liquid nitrogen and stored at −80° C. until RNA isolation. The other half was fixed in formalin and processed for paraffin sections. These were used for histopathologic grading of astrocytoma and immunohistochemistry (IHC).

Example 2

Total RNA was extracted from the frozen tissue or cell lines by using the TRI reagent (Sigma) as per the manufacturer's instructions. The RNA samples were quantified by measuring the absorbance using a spectrophotometer and visualized on a MOPS-formaldehyde gel for quality assurance. For the RNA samples used in microarray experiment, the quality and quantity was verified by using Bioanalyzer 2100 (Agilent).

MicroRNA Array Profiling

One µg total RNA from sample and reference were labeled with Hy3™ and Hy5™ fluorescent label, respectively, using the miRCURY™ LNA Array power labeling kit (Exiqon, Denmark) following the procedure described by the manufacturer. The Hy3™-labeled samples and a Hy5™-labeled reference RNA sample were mixed pair-wise and hybridized to the miRCURY™ LNA array version 10.0 (Exiqon, Denmark), which contains capture probes targeting all miRNAs for all species registered in the miRBASE version 10.0 at the Sanger Institute. The hybridization was performed according to the miRCURY™ LNA array manual using a Tecan HS4800 hybridization station (Tecan, Austria). After hybridization the microarray slides were scanned and stored in an ozone free environment (ozone level below 2.0 ppb) in order to prevent potential bleaching of the fluorescent dyes. The miRCURY™ LNA array microarray slides were scanned using the Agilent G2565BA Microarray Scanner System (Agilent Technologies, Inc., USA) and the image analysis was carried out using the ImaGene 7.0 software (BioDiscovery, Inc., USA). The quantified signals were background corrected (Normexp with offset value 10) (30) and normalized using the global Lowess (LOcally WEighted Scatterplot Smoothing) regression algorithm.

Example 3

Data Analysis

The median ratio of Hy3/Hy5 intensity for replicative spots for each miRNA was obtained after normalization. The ratio Hy3/Hy5 values were log 2 transformed. Difference in log 2 ratio for each miRNA is obtained by subtracting the log 2 ratio of a given sample from the average log 2 ratio of normals. The difference in log 2 ratio was considered in subsequent analyses. We have analyzed 7 normals, 13 AA (Grade III), 13 primary GBM (Grade IV) and 13 secondary GBM (Grade IV) by microarray hybridization. The miRNAs having values in at least 70% of the samples in each group were considered for further analysis. To find the significantly differentially regulated miRNAs between normal brain and astrocytoma and between the groups of malignant astrocytoma, data were analyzed by Significance Analysis of Microarrays (SAM). In SAM analysis, P values were obtained from permutation tests (1000 permutations in each analysis). The significant genes that were identified by SAM were subjected to Hierarchical Clustering Analysis to identify the pattern of expression across different groups. TIGR Mutiple Array Viewer software package (TMeV version 4.0) was used to perform SAM and Hierarchical Cluster Analysis (HCA).

The class prediction analysis was performed by Prediction Analysis of Microarray (PAM) using PAM package in R software (Version 2.7.1). The method of the nearest shrunken centroids was used to identify a subgroup of genes that best characterizes a predefined class (14). At threshold value of 2.3, 24 genes having non-zero difference were selected. At this threshold, the error rate for AA was 0.1538 and that of GBM was 0.0769. The probability was calculated in the test data set by 10-fold cross validation. For the selected miRNAs from SAM and PAM analysis, we performed Principal component analysis (PCA) using R package (version 2.7.1). The first three principal components identified by the program were used for plotting the graph.

Example 4

TaqMan Quantitative Real-Time PCR of the miRNAs

We used TaqMan real-time PCR method (Applied Biosystems) to measure the level of mature miRNAs. miRNA specific cDNA was made using specific stem-loop primer and diluted reverse transcription product from 10 ng total RNA was used for each real-time PCR reaction. Real-time PCR was performed using ABI 7900HT real-time PCR system. The PCR conditions are: 95° C. for 10 min, and then 15 s at 95° C. and 1 min at 60° C. for 40 cycles. U6 RNA was used as endogenous control. Delta $C_t$ values were used for the analysis. Statistical significance was tested by Mann-Whitney test using GraphPad PRISM software.

Example 5

Histopathology and Immunohistochemistry (IHC)

Histologic sections of normal brain and tumor tissues were examined by light microscopy using H&E preparation. Tumor sections of diffusely infiltrating astrocytomas were graded using the WHO grading scheme. Paraffin sections (4 ☐m) from the tumor tissue and control samples were collected on silane-coated slides for IHC. The antibodies used mainly for the purpose of subclassifying GBM cases were p53 (monoclonal: DO-7, Biogenix, diluted to 1:200) and EGFR (monoclonal: E-30, Biogenix, diluted to 1:50). For p53, antigen retrieval was done by heat treatment of the deparaffinized sections in a microwave oven for 25 to 35 min at 700 W in citrate buffer (10 mmol/L, pH 6.0). For EGFR staining, the sections were pretreated with Tris-EDTA (pH 9.0) at 600 W for 30 min. All sections were further treated with methanol and 5% hydrogen peroxide to block endogenous peroxidase followed by washes with PBS buffer (pH 7.6). Skimmed milk powder (5%) was used to block background staining for 45 min. The sections were incubated with the primary antibody overnight at 4jC. This was followed by incubation with supersensitive nonbiotin horseradish peroxidase detection system (QD440-XAK, Biogenex). 3,3¶-Diaminobenzidine (Sigma) was used as chromogenic substrate. Brain tumor samples previously characterized for overexpression of p53 and EGFR were used as positive controls. p53 and EGFR immunoreactivity was seen as nuclear and membrane cytoplasmic labelling, respectively. GBMs were classified as primary and secondary, taking into consideration mainly the clinical profile of patients. EGFR, and p53 expression status was used an adjunct to segregate these groups. The mean age of patients with primary GBM was 52 years and the mean duration of symptoms was 1 month. Uniform staining for EGFR was evident in 12/13 cases and six revealed additional p53 expression. Among secondary GBMs, the mean age of the patients was 41 years and the mean duration of symptoms was 10 months. p53 immunoreactivity was uniformly evident in 12/13 cases and none showed EGFR overexpression.

ADVANTAGES

The advantages of the present invention are:
1. It provides a useful method for diagnosing (1) Malignant Astrocytoma and Normal Brain sample, (2) Glioblastoma and Anaplastic astrocytoma, (3) Secondary Glioblastoma. and Primary Glioblastoma, (4) Progressive pathway and de novo pathway.
2. Hence, it is possible to decide the most appropriate therapy.

We claim:
1. A method for distinguishing between a glioblastoma and an anaplastic astrocytoma, comprising determining the level of expression of the miRNAs in Table 6 in a test sample from a tissue suspected of being a glioblastoma or an anaplastic astrocytoma, and determining if the level is that expected of a glioblastoma or the level expected from an anaplastic astrocytoma, wherein the miRNAs in Table 6 are hsa-miR-126, hsa-miR-21, hsa-miR-146b-5p, hsa-miR-155, hsa-miR-16, hsa-miR-193a-3p, hsa-miR-199a-3p/hsa-miR-199b-3p, hsa-miR-22, hsa-miR-335, hsa-miR-143, hsa-miR-381, hsa-miR-24, hsa-miR-552, hsa-miR-886-5p, hsa-miR-142-5p, hsa-miR-34a, hsa-miR-128, hsa-miR-923, hsa-miR-513a-5p, hsa-miR-509-3-5p, hsa-miR-376c, hsa-miR-886-3p, hsa-miR-219-2-3p, hsa-miR-451.

2. The method of claim 1, wherein determining the level of expression of the miRNAs comprises a nucleic acid based detection method.

3. The method of claim 2, wherein the detection method comprises in situ hybridization or RT-qPCR analysis.

4. The method of claim 1, wherein a decrease in the level of hsa-miR-219-2-3p, or an increase in the level of the other miRNAs in Table 6, in the test sample is indicative of a glioma rather than an anaplastic astrocytoma.

5. A kit for distinguishing a glioblastoma from an anaplastic astrocytoma, comprising nucleic acid probes complementary to the miRNAs in Table 6, and instructions for using said kit for distinguishing a glioblastoma from an anaplastic astrocytoma, wherein the miRNAs in Table 6 are hsa-miR-126, hsa-miR-21, hsa-miR-146b-5p, hsa-miR-155, hsa-miR-16, hsa-miR-193a-3p, hsa-miR-199a-3p/hsa-miR-199b-3p, hsa-miR-22, hsa-miR-335, hsa-miR-143, hsa-miR-381, hsa-miR-24, hsa-miR-552, hsa-miR-886-5p, hsa-miR-142-5p, hsa-miR-34a, hsa-miR-128, hsa-miR-923, hsa-miR-513a-5p, hsa-miR-509-3-5p, hsa-miR-376c, hsa-miR-886-3p, hsa-miR-219-2-3p, hsa-miR-451.

6. A method for distinguishing between a gliomablastoma and an anaplastic astrocytoma, comprising determining the level of expression of the miRNAs listed in Table 6 in a test sample from a tissue suspected of being a glioblastoma or an anaplastic astrocytoma, using a kit comprising nucleic acid probes complementary to the miRNAs in Table 6, wherein the miRNAs in Table 6 are hsa-miR-126, hsa-miR-21, hsa-miR-146b-5p, hsa-miR-155, hsa-miR-16, hsa-miR-193a-3p, hsa-miR-199a-3p/hsa-miR-199b-3p, hsa-miR-22, hsa-miR-335, hsa-miR-143, hsa-miR-381, hsa-miR-24, hsa-miR-552, hsa-miR-886-5p, hsa-miR-142-5p, hsa-miR-34a, hsa-miR-128, hsa-miR-923, hsa-miR-513a-5p, hsa-miR-509-3-5p, hsa-miR-376c, hsa-miR-886-3p, hsa-miR-219-2-3p, hsa-miR-451.

7. The method of claim 6, wherein determining the level of expression of the miRNAs comprises a nucleic acid based detection method.

8. The method of claim 7, wherein the detection method comprises in situ hybridization or RT-qPCR analysis.

9. The method of claim 6, wherein a decrease in the level of hsa-miR-219-2-3p, or an increase in the level of the other miRNAs in Table 6, in the test sample is indicative of a glioma rather than an anaplastic astrocytoma.

* * * * *